US00PP22904P3

(12) United States Plant Patent
Doll

(10) Patent No.: US PP22,904 P3
(45) Date of Patent: Jul. 31, 2012

(54) ***HYDRANGEA* PLANT NAMED 'DOLKIS'**

(50) Latin Name: ***Hydrangea* hybrid**
Varietal Denomination: DOLKIS

(76) Inventor: Marie-France Doll, La Foret Fouesnant (FR)

( * ) Notice: Subject to any disclaimer, the term of this patent is extended or adjusted under 35 U.S.C. 154(b) by 0 days.

(21) Appl. No.: 12/928,141

(22) Filed: Dec. 2, 2010

(65) Prior Publication Data

US 2012/0144538 P1 Jun. 7, 2012

(51) Int. Cl.
*A01H 5/00* (2006.01)

(52) U.S. Cl. ..... Plt./250

(58) Field of Classification Search ..... Plt./250
See application file for complete search history.

(56) References Cited

OTHER PUBLICATIONS

Upov Plant Variety Database 2011. Search for cultivar Dolkis. p. 1.*

* cited by examiner

*Primary Examiner* — Annette Para
(74) *Attorney, Agent, or Firm* — Cassandra Bright

(57) ABSTRACT

A new and distinct *Hydrangea* cultivar named 'DOLKIS' is disclosed, characterized by lacecap panicles having large white petals with pink margins and distinctive coloration to the young foliage of brown tinged with green. Flowers appear earlier than most *Hydrangea macrophylla* varieties, and the plant shape is rounded with good branching and moderate vigor. The new variety is a *Hydrangea*, normally produced as an ornamental plant for containers or gardens.

1 Drawing Sheet

Latin name of the genus and species: *Hydrangea* hybrid.
Variety denomination: 'DOLKIS'.

BACKGROUND OF THE INVENTION

The new cultivar was discovered as a result of a planned breeding program directed by the inventor, Marie-France Doll a citizen of France. Seed was bulk collected in 2001 from unpatented, unnamed plants of *Hydrangea serrata* and *Hydrangea macrophylla* and subsequently planted. Due to the bulk seed collection, exact parents are unknown. The new variety was discovered as a seedling in 2004, by the inventor in a non commercial outdoor production area in La Foret Fouesnant, France.

Asexual reproduction of the new cultivar 'DOLKIS' by vegetative cuttings was first performed in 2004, at a research nursery in Angers, France. 'DOLKIS' was first commercially available in 2010. Multiple generations have since been produced and have shown that the unique features of this cultivar are stable and reproduced true to type in successive generations.

SUMMARY OF THE INVENTION

The cultivar 'DOLKIS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DOLKIS' These characteristics in combination distinguish 'DOLKIS' as a new and distinct *Hydrangea* cultivar:

1. Lacecap panicles with large white petals with pink margins
2. Brown young foliage tinged with green 3. Early blossoming in the *Hydrangea macrophylla* group
4. Rounded shape plant and good branching
5. Moderate vigor
6. Darker foliage color in the Fall

COMMERCIAL COMPARISON

'DOLKIS' can be compared to the commercial variety *Hydrangea serrata* 'Kiyosumi' unpatented. The two varieties are similar in most horticultural characteristics however, plants of 'DOLKIS' have stronger, thicker branches and flowers that last longer on the plant. Additionally, 'DOLKIS' has larger petals.

The new variety can also be compared to the commercial variety *Hydrangea macrophylla*, 'Love You Kiss', unpatented. *Hydrangea* 'DOLKIS' and *Hydrangea* 'Love You Kiss' are similar in most horticultural characteristics, however, plants of 'DOLKIS' are less vigorous, but produce more branches and a denser plant. Additionally, 'Dolkis' produce sterile flowers per inflorescence.

BRIEF DESCRIPTION OF THE PHOTOGRAPH

The accompanying photograph in FIG. 1 illustrates in full color a typical plant of 'DOLKIS' grown in a outdoors, in Angers, France, in a commercial 3 liter container. Age of the plant photographed is approximately 2 years. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DOLKIS' plants grown outdoors, in Angers, France. The growing temperature ranged from approximately 10° C. to 35° C. daytime and 5° to 15° C. at night. Measurements and numerical values represent averages of typical plant types. Measurements were taken during the Fall.

Botanical classification: *Hydrangea* hybrid 'DOLKIS'.

PROPAGATION

Time to initiate roots: Approximately 3 weeks at approximately 20° C.

Root description: Fine, fibrous.

Root color: Near RHS White 155A.

Propagation method: Vegetative cuttings.

PLANT

Age of plant described: 24 months.

Growth habit: Flowering perennial shrub. Round, well branched.

Height: Approximately 60 cm.

Plant spread: Approximately 55 cm.

Growth rate: Moderate.

Branching characteristics: Very good free branching.

Length of lateral branches: Approximately 20 cm.

Number of lateral branches: Approximately 15.

Diameter of lateral branches: Approximately 1 cm.

Lateral branch shape: Round.

Lateral branch strength: Moderate.

Lateral branch color: Near RHS Yellow-Green 146B slightly tinged at the nodes with RHS Greyed-Purple 183A.

Other stem or plant characteristics: Stems densely covered with lenticels.

*Lenticel length*.—Approximately 0.75 to 1.25 cm.

*Lenticel width*.—Approximately 0.5 to 0.1 cm.

*Lenticel color*.—Near RHS Greyed-Purple 183 A.

Number of leaves per lateral branch: Approximately 10.

Age of plant described: 24 months Approximately.

FOLIAGE

Leaf:

*Arrangement*.—Opposite.

*Compound or single*.—Single.

*Average length*.—Approximately 13 to 14 cm.

*Average width*.—Approximately 6 to 7 cm.

*Shape of blade*.—Ovate to elliptic oblong.

*Apex*.—Acute to long-tapering.

*Base*.—Asymmetric to very lightly asymmetric.

*Attachment*.—Petiole attached to leaf lamina.

*Margin*.—Serrate, approximately 1.5 to 2 teeth per cm.

*Texture and appearance of top surface*.—Moderately glossy, non-pubescent.

*Texture and appearance of bottom surface*.—Matte, non-pubescent.

*Leaf internode length*.—Approximately 4 to 5 cm.

*Color*.—Young foliage upper side: Near RHS Brown 200A and 200B, both colors present tinged with Yellow-Green 146D. Young foliage under side: Near RHS Yellow-Green 146 C tinged with Brown 200C. Mature foliage upper side: Near RHS Yellow-Green 146A, 146B, 146C, all colors present individually. Mature foliage under side: Near RHS Yellow-Green 146B.

*Venation*.—Type: arcuate to pinnate. Venation color upper side: Near RHS Yellow-Green 145C. Venation color under side: Near Yellow-Green 145C.

*Durability of foliage to stresses*.—Good resistance to physical stress.

Petiole:

*Average length*.—Approximately 1.5 cm.

*Diameter*.—Approximately 0.3 to 0.4 cm.

*Color*.—Near RHS Yellow-Green 146D, slightly tinged at the nodes Greyed-Purple 184A.

FLOWER

Bloom period:

*Natural season*.—Continuous June through August.

Inflorescence:

*Arrangement*.—Single, sterile and fertile flowers arranged in terminal lacecap type panicles.

*Quantity of flowers per inflorescence*.—Fertile flowers, 200 approximately. Sterile Flowers, 10 to 15 approximately.

*Persistent or self-cleaning*.—Persistent.

*Fragrance*.—No.

Sterile flower:

*Diameter of entire flower*.—Approximately 5.5 cm.

*Depth of flower*.—Approximately 1 cm.

Petals:

*Length of petal*.—Approximately 2.7 cm.

*Width of petal*.—Approximately 1.3 cm.

*Apex*.—Acute.

*Shape of petal*.—Broadly deltoid.

*Petal margin*.—Slightly serrate.

*Petal arrangement*.—Rotate, slightly overlapping.

*Petal number*.—4 to 5.

*Petals fused*.—No.

*Petal texture*.—Smooth.

*Color*.—Upper surface at first opening: Near RHS Green-White 157D with margin near Red 51A. Upper surface at maturity: Near RHS White 155B with margin near Red 51A. Upper surface at fading: Near RHS Red-Purple 65D. Under surface at first opening: Near RHS Green-White 157D with margin near Red 51A. Under surface at maturity: Near RHS White 155B with margin near Red 51B. Under surface at fading: Near RHS White 155B with margin near Red 51B. No Petaloids present.

OTHER CHARACTERISTICS

Disease resistance: Neither resistance nor susceptibility to diseases or pests has been observed in this variety.

Drought tolerance and cold tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.

Fruit/seed production: No fruits/seeds detected to date.

What is claimed is:

1. A new and distinct cultivar of *Hydrangea* plant named 'DOLKIS' as herein illustrated and described.

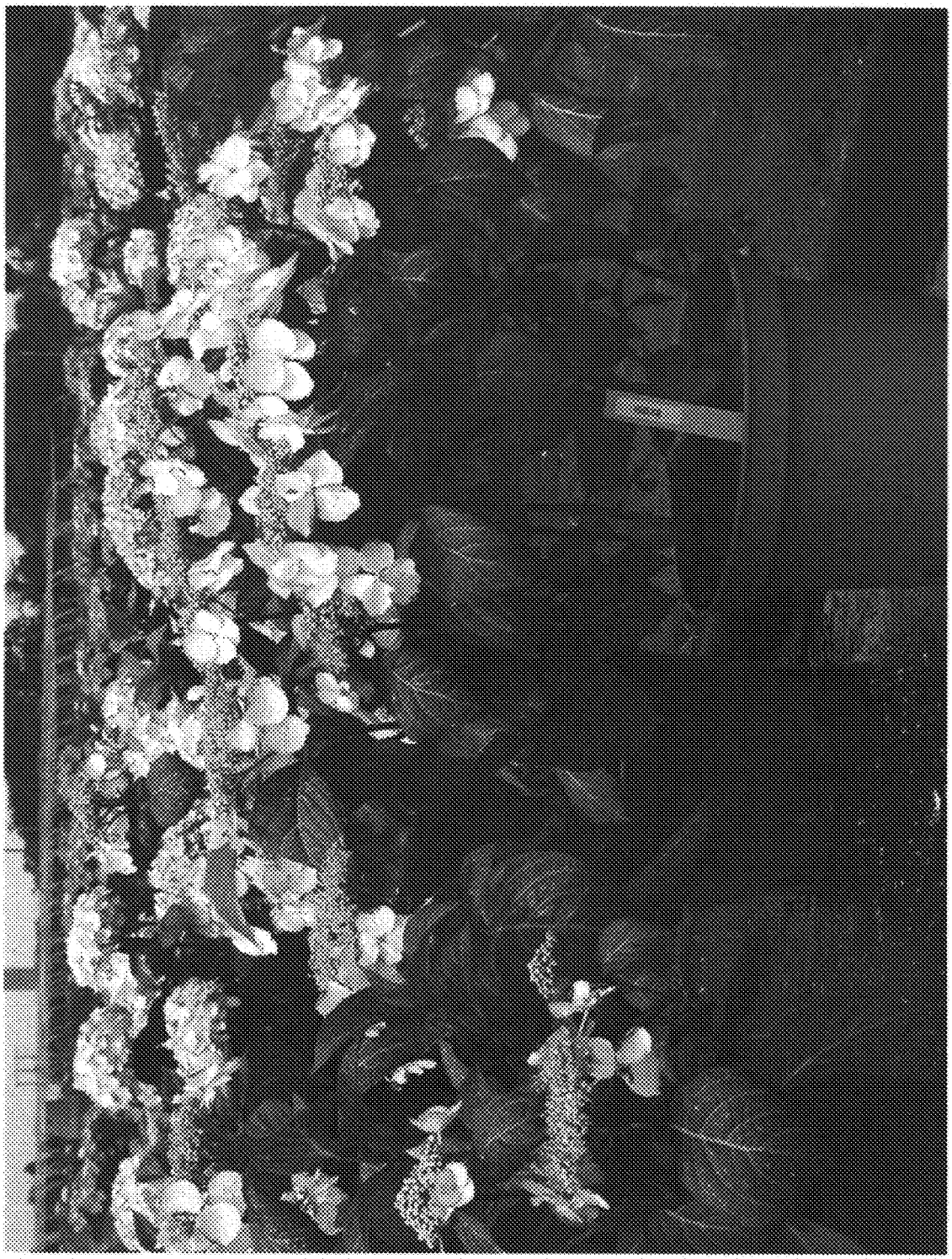

* * * * *